United States Patent [19]

Meyer

[11] Patent Number: 4,669,321

[45] Date of Patent: Jun. 2, 1987

[54] SAMPLE TAKING DEVICE

[76] Inventor: Pio Meyer, Sagenrainstr. 7, 8636 Wald, Switzerland

[21] Appl. No.: 845,831

[22] Filed: Mar. 6, 1986

[51] Int. Cl.⁴ .............................................. G01N 1/10
[52] U.S. Cl. ................................................. 73/863.85
[58] Field of Search ......................... 73/863.85, 863.86

[56] References Cited

U.S. PATENT DOCUMENTS

| 2,815,663 | 12/1957 | Zupfer | 73/863.85 X |
| 3,747,411 | 7/1973 | McDermott et al. | 73/863.85 X |
| 4,096,754 | 6/1978 | Beveridge, Jr. et al. | 73/863.85 X |
| 4,562,747 | 1/1986 | Jaeger | 73/863.85 X |

FOREIGN PATENT DOCUMENTS

| 2752284 | 6/1978 | Fed. Rep. of Germany | 73/863.86 |
| 2907558 | 8/1980 | Fed. Rep. of Germany | 73/863.85 |
| 56876 | 3/1969 | Poland | 73/863.86 |
| 2108004 | 5/1983 | United Kingdom | 73/863.86 |
| 549706 | 3/1977 | U.S.S.R. | 73/863.86 |

Primary Examiner—Stewart J. Levy
Assistant Examiner—Tom Noland
Attorney, Agent, or Firm—David M. Ostfeld

[57] ABSTRACT

A sample taking device comprised of three parts which are axially moveable with respect to each other: the main rod (7), a taking tube (10) and the flask holder (27). Through a tube (9) arranged on the main rod (7) a sterilizing medium, for example vapor, is introduced and flows throughout the whole device and comes out through the tube (29). By the action of an axial force on the cup (31) the needle (36) traverses the plug (35); if the force is intensified, the taking tube (10) is pushed in response to the force of the pre-strained pressure spring (15) into the culture medium (2) which may then flow into the flask (32). At the end of the sample taking, the device may be rinsed and re-sterilized, without the need for adding or dismounting certain parts. The device is also appropriate for the sample taking of pathogen cultures.

8 Claims, 5 Drawing Figures

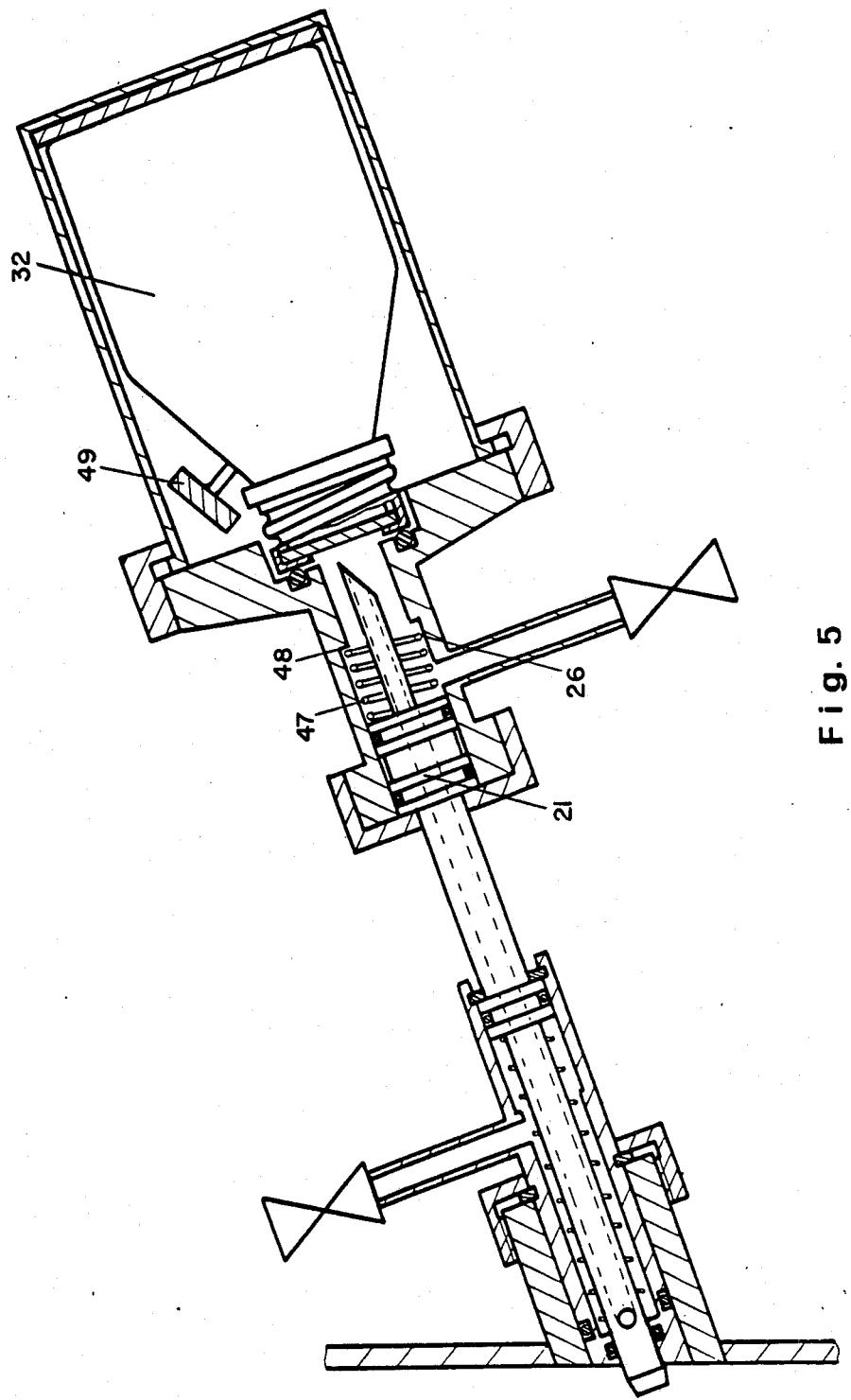

SAMPLE TAKING DEVICE

BACKGROUND OF THE INVENTION

1. Field of the Invention

The present invention refers to a device for taking samples from e.g. bio-reactors or fermentors, chemical reactors, and storage vessels and for drawing off these samples into sterile receptacles.

2. Description of the Related Art

Taking samples from cultures out of a fermentor generally is indicated whenever the process parameters e.g. pH, $pO_2$, $pCO_2$, temperature, viscosity, and others are insufficient for interpreting the state within the cultured cells. This is the reason the desire for a sample taking device is as old as the technique of fermentation in closed vessels. To draw off the taken probe into a sterile receptacle is always mandatory when germs occasionally present in the receptacle could contaminate the probe. Therefore devices are known in the art, e.g. from the Swiss Pat. No. 629 591.

In this mentioned patent specification, which represents the state of the art, a device is described consisting of a sampling tube, a valve—e.g. a corner valve—and a bellshaped support for the sterile receptacle. The sampling tube is fastened to an outlet in the fermentor by means of a thread or by a flange. From the opened corner valve the culture broth flows through a first-longer-needle, which penetrates the elastomeric stopper of the sterile receptacle, into this said receptacle. The air contained within the receptacle is vented through a second-shorter-needle, which as well penetrates the said stopper. The difficulties of this and similar devices are encountered with their sterilization in a threefold way:

If one is assuming that the insides of the sampling tube, of the corner valve, and of the longer needle have been sterilized together with the fermentor before the fermentation has been started, sterility cannot be guaranteed, because the outside of the stopper is exposed to the non sterile air of the laboratory.

After the first sample has been taken and the receptable has been removed, the needle and the corner valve as well as the valve seat are not sterile any more and also cannot be sterilized any more.

Furthermore the sampling tube generally is contaminated with remainders of the culture broth. In case pathogenic cultures have been cultured in the fermentor germs enter the laboratory as soon as the receptacle is taken off the needle.

Other known devices work with a cup being put on to the needle during sterilization by steam and being taken away after sterilization is terminated. All the same, contamination of the sample and of the laboratory remains possible.

SUMMARY OF THE INVENTION

The problem to be solved by the present invention was to create a sample taking device which can be sterilized as well together with the fermentor as in situ, which can be rinsed after each drawing-off of a sample and again be sterilized, and which is designed such as to allow for sterilization of the outside of the stopper of the sterile drawing-off receptacle together with the rest of device, so that the device can equally be used for taking samples of pathogenic cultures with these samples never getting into contact with the surrounding atmosphere.

The solution of this problem is characterized by the presence of three main components, namely a hollow main shaft fastened to the container from which the sample is to be taken, a sampling tube, coaxially movable within the hollow main shaft, and a support or bottle holder for the receptacle, axially movable with respect to the said sampling tube; further characterizing features are two pipes, one at the hollow main shaft, one at the said support, a front end closure and a lateral opening at the sampling tube and the shaping of the sampling tube as a needle at its end opposite to the closure, in order that the sterilizing means can enter the pipe at the hollow main shaft from where it flows through the lateral opening into the sampling tube, through the needle into the bottle holder, leaving it through the second pipe. In the sampling position of the device, which is effected by applying an axial force onto the device, the liquid or broth to be sampled is flowing through the sampling tube—the lateral opening of which now reaches into the inside of the container——and the needle, which now penetrates the stopper of a drawing-off receptacle contained within the bottle holder, into said receptacle.

BRIEF DESCRIPTION OF THE DRAWINGS

By means of the accompanying drawings, embodiments of the invention are described in detail.

They show.

DESCRIPTION OF THE PREFERRED EMBODIMENTS

Figure 1:
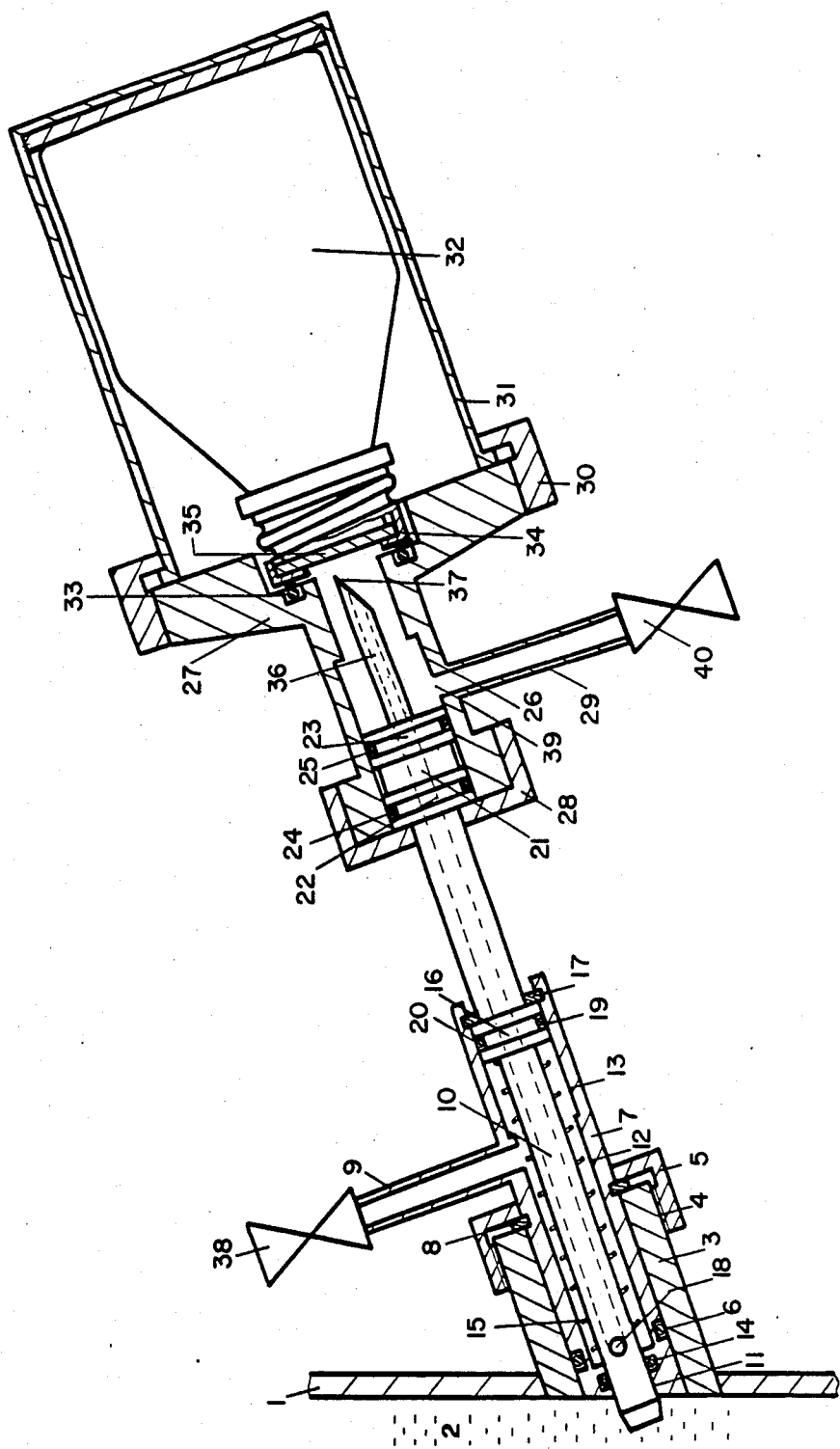
FIG. 1 a longitudinal cross section through a sample taking device according to this invention, fastened to a fermentor, FIG. 2 the embodiment according to FIG. 1 in working position I, FIG. 3 the same embodiment, in working position II, FIG. 4 a second embodiment of this invention, again in longitudinal cross section, FIG. 5 a modification of the first embodiment.

A fermentor, whose wall 1 is shown in FIG. 1, contains a culture broth 2. A normal feed pipe 3 is welded to the wall 1, the pipe 3 carrying a thread 4 for a screw cap 5. The hollow main shaft 7 of the sample taking device is inserted into the normal feed pipe 3 and tightened by means of an O-ring 6. The screw cap 5 secures the hollow main shaft 7 against retraction by pressing against a ring 8 at the shaft 7. A further pipe 9 opens into the hollow main shaft 7, which pipe 9 carries a valve 38 controlling the flow of the sterilizing fluid. A movable sampling tube 10 fits into the hollow main shaft 7. The latter therefore exhibits three bores 11,12,13 of different width:

A bore 11 of such width as to seal tightly against the culture broth 2 by means of an O-ring 14 sunken in the front end of the main shaft 7, and the sampling tube 10, a bore 12, wider than the bore 11, of such width that a compression spring 15, surrounding the sampling tube 10 can be moved with enough clearance within the hollow main shaft 7 without touching the latter;

a bore 13, again wider than the bore 12 allowing for the axial travel of a guide ring 16, a travel which is limited to the rear—away from the fermentor—by a further ring 17.

The sampling tube 10 is closed at its front end facing the fermentor. More to the rear it carries a lateral bore 18 as an inlet to its interior. The guide ring 16 is fastened to the sampling tube 10 and carries a groove 19 with an O-ring 20 for sealing purposes. The compression spring 15 is mounted with initial stress and retracts the sampling tube 10 into the hollow main shaft 7 provided no external force is applied.

A further guide ring 21 is fastened to the sampling tube 10 as well. It carries two grooves 22,23 with an O-ring 24,25 each. The O-rings 24,25 make up for a seal together with a bore 26 in a component called bottle holder 27.

The guide ring 21 is secured against retraction by means of a screw cap 28. A pipe 29 opens into the bore 26 which pipe 29 operates as a vent for the sterilizing means, for the rinsing fluid, or as condensation run-off depending on what is fed to the pipe 9. By means of a further screw cap 30 a cup 34 is fastened to the bottle holder 27 which cup 31 presses a bottle 32, receptacle for the culture samples, against an O-ring 33. This said O-ring 33 makes up for a seal together with the screw cover 34 of the bottle 32, this screw cover 34 holding down a suitably shaped stopper 35 made from an elastic material. The bottle 32 is tightly sealed by said stopper 35. The end of the sampling tube 10 adjacent to the bottle 32 carries a needle 36 tapered to a tip 37.

In this position of the sample taking device there is a continuous connection from pipe 9 to pipe 29: The sterilizing means, e.g. steam, flows through the pipe 9, flows around the sampling tube 10 the compression spring 15 included, gets into the interior of the sampling tube 10 through the lateral bore 18 and leaves the sampling tube 10 at the tip 37 of the needle 36. The interior of the bottle holder together with the area of the screw cover 34 and of the stopper 35 uncovered by the O-ring 33 and limited by the O-ring 25 are also acted upon by the steam and therefore become sterilized. Steam and condensate leave the device by the pipe 29. All parts of the device which later get into contact with the culture sample now are sterile.

After termination of the sterilization the valve 38 is closed just as well as a further valve 40 at the pipe 29, and a force is applied upon the bottom of the cup 31 acting in the direction of the sampling tube 10. This force is moving the bottle 32 towards the tip 37 now penetrating the stopper 35. At the same time the O-ring 25 travels across the opening 39 of the pipe 29 which now lies between O-rings 24 and 25; now the tip 37 of the needle 36 has penetrated the stopper 35 and the guide ring 21 has reached the end of the bore 26.

Figure 2:
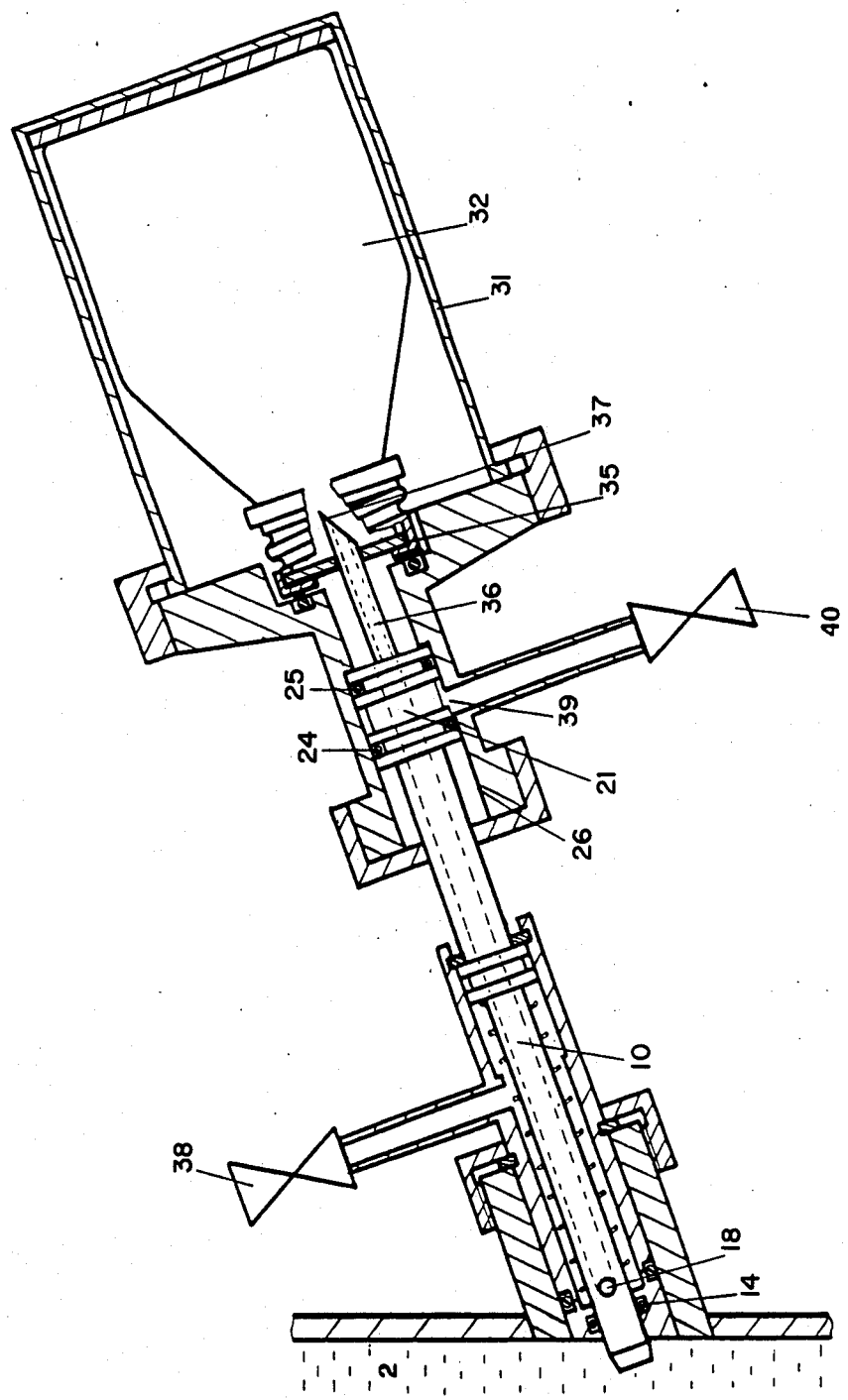

This situation is shown in FIG. 2 as working position I. It is only a through position for the working position II shown in FIG. 3, at the same time also a through position from the working position II back to the sterilizing position according to FIG. 1, where the screw cap 30 can be unscrewed and the bottle 32 be taken out of the cup 31. This operation generally will be preceded by rinsing and, in case of pathogenic cultures, by sterilization.

In case the abovementioned force upon the bottom of the cup 31 is further increased, the sampling tube 10 is pushed through the O-ring 14 into the culture broth 2. As soon as the lateral bore 18 is freed by the O-ring 14 this culture broth 2 enters the sampling tube 10 and, through the needle 86, also the bottle 32. Although in the embodiment according to FIGS. 1 through 3 no venting of the bottle 32 is provided for, the culture broth 2 can enter the bottle 32 because the fermentor holds a slight overpressure or such easily can be obtained; furthermore the pressure in the bottle 32 generally will be below atmospheric pressure due to the preceding sterilisation. This reduced pressure will only little be compensated for when the needle 36 enters the bottle 32 because of the volume of the whole sample taking deviced being small compared with the volume of the bottle 32.

Figure 4:
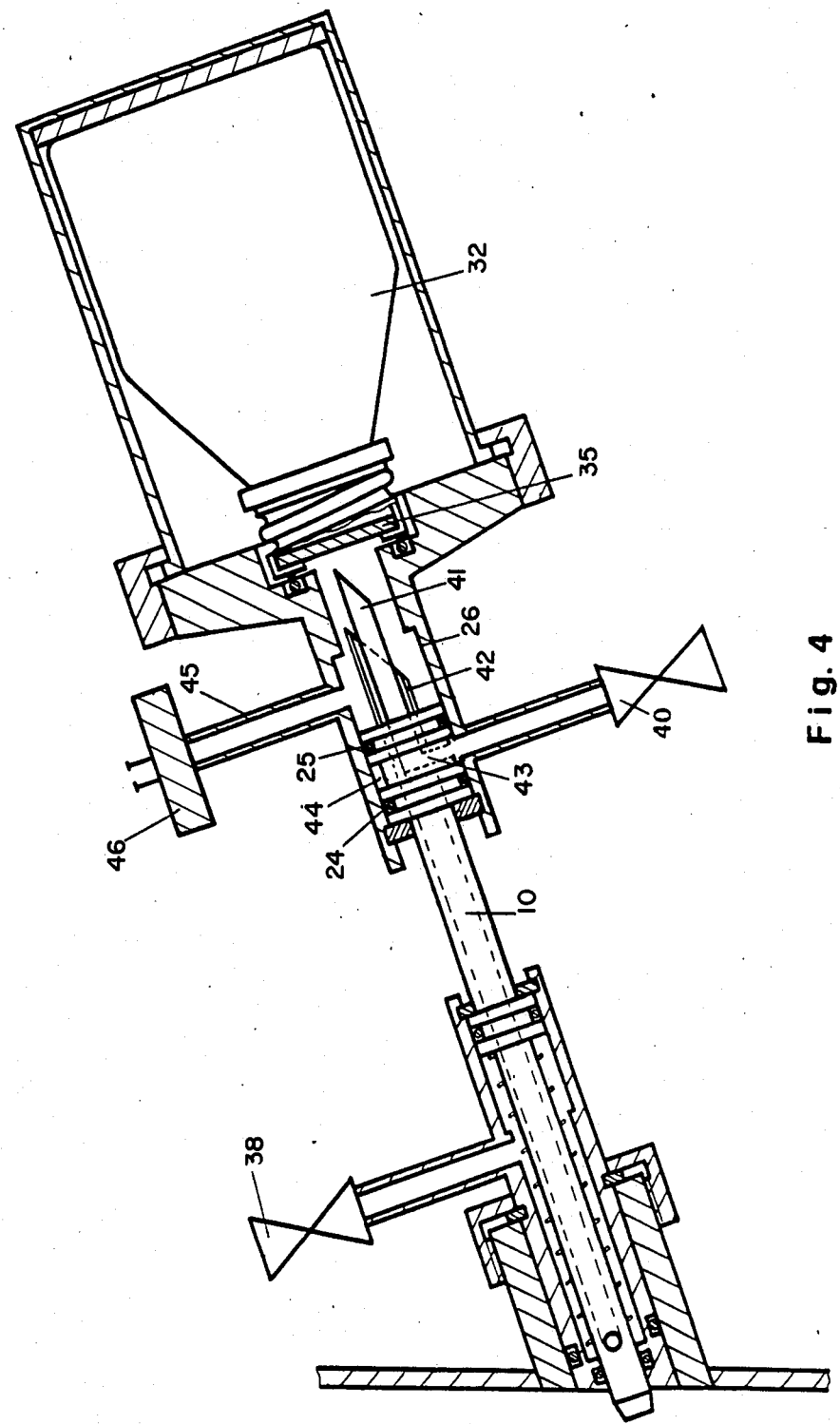

To use this embodiment of the invention in connection with bio-reactors or fermenters is only one of its many possible applications. It is as well suitable to take samples from chemical reaction vessels with liquid or gaseous content as from storage tanks with a content which is chemically and/or biologically unstable. In case samples are to be taken from vessels at atmosphere pressure and drawn off into bottles without at least a partial vacuum, venting of the bottle 32 becomes necessary. FIG. 4 shows such an embodiment of the invention. Here are two concentric needles 41,42, instead of the needle 36. The inner needle 41 is connected to the groove 44 between the O-rings 24 and 25 by way of a bore 43. In the position of the device according to FIG. 4—the sterilizing position—the valves 38 and 40 may be opened and steam flows, as shown before, through the sampling tube 10 and the outer needle 42 into the space within the bore 26. Through the needle 41 the steam is flowing back via the bore 43 into the pipe 29 where it is vented. With respect to the embodiment according to FIGS. 1 till 3 the pipe 29 is offset towards the fermentor. In the working position I (not shown for this embodiment of the invention) both needles 41,42, penetrate the stopper 35 one after the other. The groove 44 now is positioned in front of another pipe 45 which leads into a filter 46 suited for holding back microorganisms but permeable for air.

Figure 3:
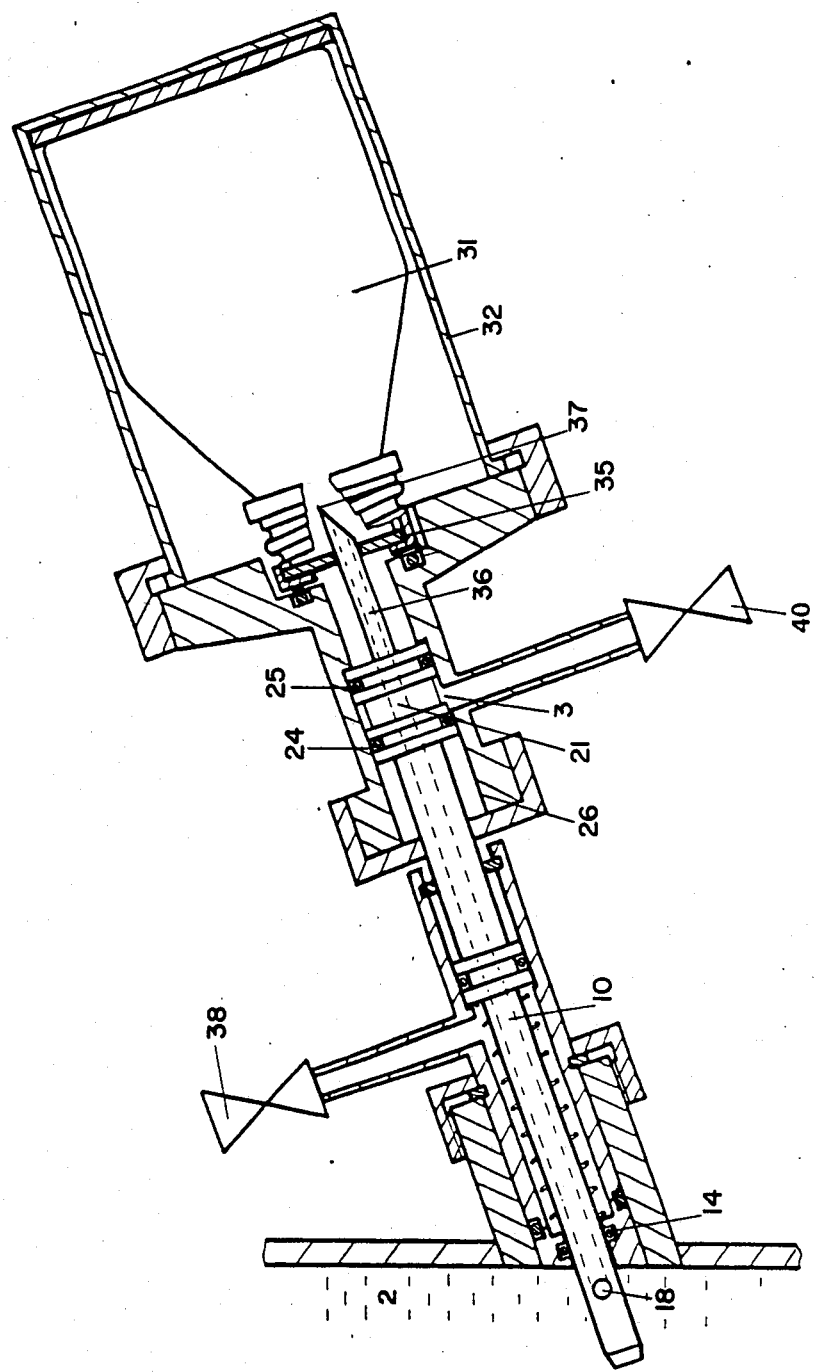

In the working position II which again can be taken from FIG. 3 culture broth enters the bottle 32 by way of the outer needle 42; the displaced air leaves the bottle 32 through the needle 41, gets into the groove 44, through the bore 43, then it enters the pipe 45, passes the filter 46 from where it gets into the open air or into a suitable receptacle or a monitoring device (both not shown).

It is also contained in the idea of the invention to interchange the function of the two needles 41 and 42 in as much as the needle 41 is in direct connection with the inside of the sampling tube 10 and the vented air leaves through the needle 42 which, for this purpose, is connected to the bore 43.

In FIG. 5 there is shown a further embodiment of the invention. It differs from the embodiment shown in FIG. 1 as follows: There is a second pre-stressed compression spring 47 inserted into the bore 26 pressing against both the guide ring 21 and a shoulder 48 at the bore 26. This compression spring 27 is weaker than the compression spring 15, such as it is completely compressed before the compression of the spring 15 begins. A further difference with respect to the embodiment of FIG. 1 is a filter 49 connected directly to the bottle 32; this is e.g. a glass filter with the features named for the filter 46. Containing this said compression spring 47 the whole apparatus can be operated by simply increasing or decreasing the axial force described for FIGS. 1 till 3; no inversion of the direction of the force is necessary. Hence a unidirectional linear drive (electrical or pneumatical) is suitable for this operation. The valves 38, 40 can be e.g. solenoid valves. In case the screw cap 30 is replaced by a (not shown) remotely controlled slide lock, taking samples can easily be automated.

What we claim is:

1. A device for taking samples from vessels like bioreactors or fermentors, chemical reactors, and storage tanks, characterized
    by a hollow main shaft (7) to be fastened to the vessel, with a pipe (9) as an inlet for a sterilizing means, a guide ring (16) in a sampling tube (10) which is axially movable within the hollow main shaft (7), a bottle holder (27) again axially movable with respect to the sampling tube (10) by means of a further guide ring (21) travelling in a bore (26) of the bottle holder (27),
    in that the sampling tube (10) which is closed at its front end towards the vessel has a lateral bore (18) which opens into the interior of said sampling tube 10,
    in that the rear end of the sampling tube (10) carries a needle with a tip,
    by at least one further pipe (29), the opening (39) of which leads into the bore (26) of the bottle holder (27) for venting the sterilizing means fed to the pipe (9),
    by a first O-ring (14) pressing against the exterior of the sampling tube (10) and sealing the interior of the hollow main shaft (7) against the vessel, a second O-ring (20) sitting in a groove (19) of the guide ring (16) and sealing the interior of the hollow main shaft against the external laboratory or test site environment, hereinafter called "the Laboratory", two identical O-rings (24,25) sitting in two grooves (22,23) of the guide ring (21) and sealing the laboratory against the interior of the bottle holder (27), and a further O-ring (33) pressed between the bottle holder (27) and the screw cover (34) of the bottle (32) sealing the interior of the bottle holder (27) against the laboratory,
    in that the axial travel of the guide ring (21) which is fastened to the sampling tube (10) is such as to allow for the sterilizing means flowing out of the needle to reach the whole interior of the bottle holder (27) and to leave it by the pipe (23), when the said guide ring (21) is at its one end position, and at its other end position the guide ring (21) is closing the opening (39) of the pipe (29) and the needle has penetrated the stopper (35) of the bottle (32),
    in that the axial travel of the sampling tube (10) within the hollow main shaft (7) is such as to reach as far into the vessel that the culture broth (2) can enter the lateral bore (18) in the one end position, and in the other end position the said sampling tube (10) is wholly within the hollow main shaft (7) except for possibly a frontmost portion of the closed front end thereof.

2. A sample taking device according to claim 1, characterized by a prestressed compression spring (15) being within and coaxial to the hollow main shaft (7) and the sampling tube (10), this said spring (15) pressing with one end against the hollow main shaft (7) with the other end against the guide ring (16) which is fastened to the sampling tube (10), this said spring (15) being dimensioned such as to retract as much as possible of the sampling tube (10) out of the vessel when an external force acting axially upon the device is eliminated.

3. A sample taking device according to claim 2, characterized by a prestressed compression spring (47) within the and coaxial to the bottle holder (27) as well as being coaxial to the needle, which spring (47) presses with its one end against a shoulder (48) at the interior of the bottle holder (27), with its other end against the guide ring (21), and being so dimensioned that the axial force necessary for its compression remains smaller than the force necessary to initiate compression of the compression spring (15).

4. A sample taking device according to one of the claims 1, 2, or 3, characterized
    by a second needle having an additional tip whereby one of the needles is directly connected to the sampling tube (10), the other one of the needles is connected to a groove (44) between two O-rings (24,25) by way of a bore (43),
    by a further pipe (45) opening into the bore (26) to which pipe (45) a filter (46) is connected,
    in that the axial travel of the guide ring (21) is such as to allow for the sterilizing means to reach the whole interior of the bottle holder (27) and to leave it by the other of the needles, the bore (43), the groove (44), and the pipe (29) when it is in its one end position, and when it is in its other end position the two needles have penetrated the stopper (35) of the bottle (32), and the air contained in the bottle (32) is vented through the one of the needles which is directly connected to the sampling tube (10), through the bore (43), the groove (44), the tube (45), and the filter (46).

5. A sample taking device according to claim 4 characterized by the two needles being concentric, one of the needles being an inner needle being connected directly to a groove (44).

6. A sample taking device according to claim 4 characterized by the outer needle being connected directly to the sampling tube (10).

7. A sample taking device according to claim 6, characterized by the inner needle being longer than the outer needle.

8. A sample taking device according to one of the claims 1, 2, or 3, characterized by a filter (49) connected to the bottle (32) for venting any air displaced therefrom when a sample collects therein.

* * * * *